United States Patent [19]

Patterson

[11] 4,071,476

[45] Jan. 31, 1978

[54] DETERGENT BUILDERS AND COMPOSITION CONTAINING THE SAME

[75] Inventor: John A. Patterson, Fishkill, N.Y.

[73] Assignee: Texaco Inc., New York, N.Y.

[21] Appl. No.: 728,095

[22] Filed: Sept. 30, 1976

Related U.S. Application Data

[62] Division of Ser. No. 437,252, Jan. 28, 1974, Pat. No. 4,039,464.

[51] Int. Cl.$^2$ .......................... C11D 3/20; C11D 3/34
[52] U.S. Cl. .................. 252/557; 252/89 R; 252/135; 252/538; 252/DIG. 11; 252/DIG. 14; 560/127; 560/76; 560/190; 560/195
[58] Field of Search ............... 252/89, 548, 558, 557, 252/539, 538, DIG. 11, DIG. 14, 135; 260/475 R, 475 N, 485 R, 485 J, 484 P

[56] References Cited

U.S. PATENT DOCUMENTS

| | | | |
|---|---|---|---|
| 2,028,091 | 1/1936 | Jaeger | 260/106 |
| 3,798,183 | 3/1974 | Bruson | 252/557 |
| 3,799,970 | 3/1974 | Crutchfield et al. | 260/473 G |
| 3,812,044 | 5/1974 | Connor et al. | 252/89 |
| 3,844,982 | 10/1974 | Connor et al. | 252/544 |
| 3,915,879 | 10/1975 | Barnett | 252/89 |
| 3,920,569 | 11/1975 | Carson et al. | 252/89 |

Primary Examiner—P.E. Willis, Jr.
Attorney, Agent, or Firm—Thomas H. Whaley; Carl G. Ries; H. W. Archer

[57] ABSTRACT

Disclosed and claimed are biodegradable builders for use with water-soluble organic detergent compounds. The builders are alkali metal salts of ester-acids derived from polycarboxylic acid anhydrides.

Also claimed are a method for making the compounds and detergent compositions containing the disclosed compounds.

2 Claims, No Drawings

DETERGENT BUILDERS AND COMPOSITION CONTAINING THE SAME

This is a division, of application Ser. No. 437,252, filed Jan. 28, 1974 now U.S. Pat. No. 4,039,464.

BACKGROUND OF THE INVENTION

1. Field of the Invention

This invention relates to detergent compositions containing novel builders, to a method for making such builders, and to detergent compositions containing such builders.

2. Description of the Prior Art

Because phosphates are believed to contribute to the eutrophication of waters, considerable research efforts recently have been expended with a view of providing builders which are phosphorus free.

Phosphate-free organic builders are already known and some are disclosed in Unilever Netherlands patent application 72-06772 and in U.S. Pat. No. 3,635,830. The first of these discloses the tetrahydrate and pentahydrate of carboxymethoxysuccinate trisodium which were used separately or together as builders in detergent compositions. Undesirably, these compounds have to be treated with water-ethanol to hydrate them sufficiently to be easily handled thereby adding considerably to production costs. For its part, U.S. Pat. No. 3,635,830 discloses, as builders, salts of oxydisuccinic acid, carboxymethyloxy succinic acid and hydrofuran tetracarboxylic acid. The recited compounds required several purification steps before incorporation in detergent compositions.

SUMMARY OF THE INVENTION

The builders of the invention are the reaction products of alkali hydroxy alkyl salts with polycarboxylic acid anhydrides and can be represented by the following general formula:

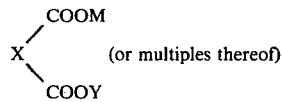

(or multiples thereof)

wherein X is

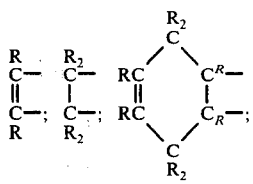

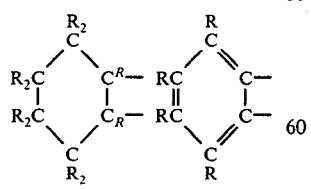

R being hydrogen, alkyl, aryl or repeating X unit;

M is an alkali metal cation including sodium, potassium, lithium or ammonium; and Y is $(CH_2)_n COOM$ or $(CH_2)_n SO_3 M$ wherein $n$ ranges from 1 to 6 and M is as before defined.

The starting materials are alkali hydroxy salts of the formula:

$$HO(CH_2)_n COOM \text{ or } HO(CH_2)_n SO_3 M$$

$n$ and M being as defined before and;
Polycarboxylic acid anhydrides of the formula:

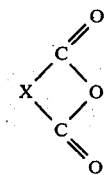

X being as defined above.

The reaction is carried out in the absence of solvent or in polar solvents which are inert to the anhydride including dioxane, dimethylformamide and methyl ethyl ketone. The reaction is carried out at temperatures of 25°–250° C. and atmospheric pressure to 1000 psi with the preferred conditions being 75°–150° C. and atmospheric pressure to 100 psi.

DISCLOSURE

For sake of simplicity the invention will be described mainly with reference to sodium carboxymethyl maleate (SCMM) which is prepared by the reaction of maleic anhydride with sodium glycolate wherein the addition is across the anhydride and apparently is followed by a neutralization step where the sodium glycolate or the adduct is the base:

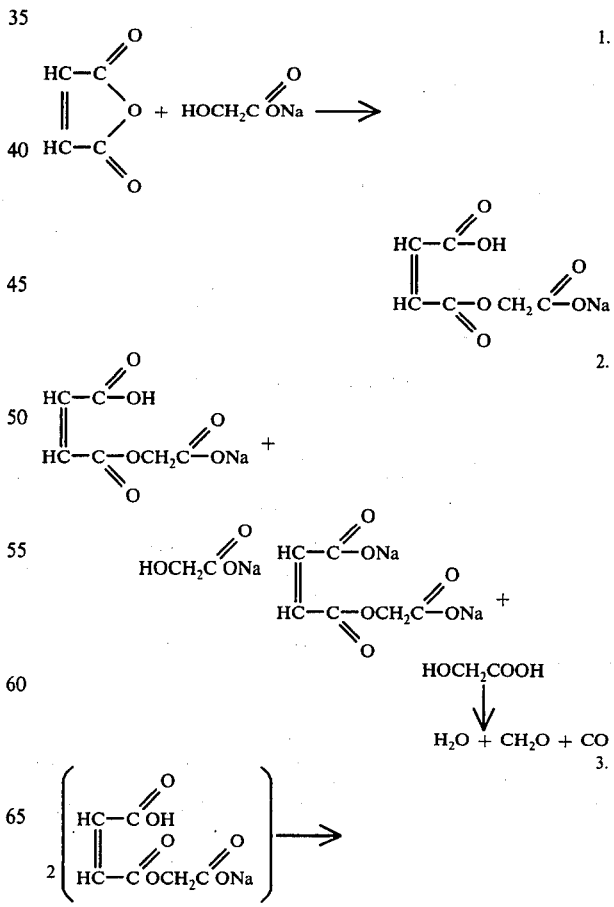

-continued

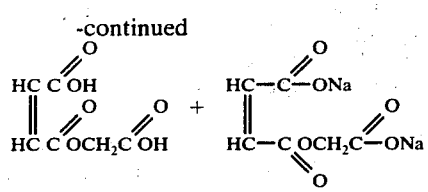

Experimental conditions are summarized in Table I. The ingredients were mixed and heated for the time indicated and worked up as outlined. In addition to small amounts of starting materials which contaminated the products, other fractions, not listed, appeared to be principally recovered starting material but in one or two cases were possibly mixed with acid or salt precursors of sodium carboxymethyloxy succinate (SCMS).

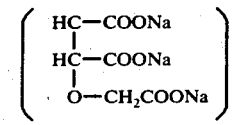

The crude sodium carboxymethyl maleate was purified from acetone, methyl ethyl ketone and/or methanol. The product was identified by nuclear magnetic resonance spectra as indicated in Table II, a quartet in the olefin region and a singlet in the $$-\overset{|}{\underset{|}{C}}-O-$$

region but shifted from the singlet for sodium glycolate. The unpurified samples also showed spectra for both maleic anhydride and sodium glycolate in varying amounts.

Sodium analyses given in Table II indicated that reactions according to Equations 2 and 3 above, probably took place.

Sample P698-31S1 was prepared by treatment with sodium methoxide assuming only Equation 1 had occurred. However, sodium analyses were little different with samples obtained without sodium methoxide neutralization and agree with the theoretical sodium content of the di-salt rather than the mono-salt (%Na=11.7).

TABLE I
PREPARATION OF SODIUM CARBOXYMETHYL MALEATE (SCMM)

| Maleic anhydride, gms. | Sodium Glycolate, gms. | Solvent Name | Ml. | Catalyst Name | gms. | Temp. °C. | Time hrs. | Work-up | Crude SCMM gms. | Run No. |
|---|---|---|---|---|---|---|---|---|---|---|
| 10 | 10 | Dioxane | 100 | Benzoyl peroxide | 0.1 | 70 | 24 | cooled, filtered | 14.4 (50%) | (875-34) |
| 10 | 10 | Dimethyl formamide | 100 | Benzoyl peroxide | 0.1 | 70 | 24 | cooled, filtered | 12 (50%) | C875-41 |
| 10 | 10 | None | — | None | — | 80–128 | ½ | cooled, extracted with acetone. Insoluble extracted with methanol. Part of methanol solution treated with sodium methoxide. | 13.5 (50%) | C875-41 |
| 20 | 20 | None | — | None | — | 100 | 1 | cooled, extracted with methanol. | 18.8 (70%) | P113-7 |
| 10 | 10 | Methyl ethyl ketone | 200 | None | — | Reflux | 24 | cooled, extracted MEK insoluble with methanol | 10.6 (90%) (MEK-CH₃OH insoluble | P113-8 |
| 10 | 9.5 | methyl ethyl ketone | 200 | None | — | Reflux | 24 | cooled, filtered | 10.6 (70%) (MEK insoluble) | P113-11 |

Value in parenthesis is approximately purity (bais NMR) of crude SCMM

TABLE II
EVALUATION OF SODIUM CARBOXYMETHYL MALEATE AND RELATED MATERIALS

| Test | SCMM Sample 1 | SCMM Sample 2 | SCMM Sample 3 | SCMS[1] | STPP[2] Standard | Maleic Anhydride | Sodium Maleate | Sodium Glycolate |
|---|---|---|---|---|---|---|---|---|
| Proton NMR (in D₂O) | δ5.8–6.8 (q2) δ4.45 (s2) | δ5.806.7 (q2) δ4.5 (s2) | δ5.8–6.7 (q2) δ4.5 (s2) | δ4.0–4.2 (ml) δ3.9 δ2.4–2.6 (m2) | — | δ6.7 (s2) | δ6.5 (s2) | δ4.0 (s2) |
| Sodium % (Found) | 19.9 | 19.8 | 21.7 | 20.9 | — | — | — | — |
| (theory) | 21 | 21 | 21 | 19.8 | — | — | — | — |
| Sap. No. (Found) | — | — | 257.8 | — | — | — | — | — |
| (theory) | — | — | 257 | — | — | — | — | — |
| Neut. No. (Found) | — | — | 14.3 | — | — | — | — | — |
| (theory) | — | — | 0 | — | — | 1150 | 0 | 0 |
| Detergency Coefficient, % | 0 | 89.2 | 85.2 | 89.7 | 100 | — | — | — |
| Identification | P698-31S1 | P113-7A | p113-105+ | P113- | | | | |

TABLE II-continued

EVALUATION OF SODIUM CARBOXYMETHYL MALEATE AND RELATED MATERIALS

| Test No. | SCMM Sample 1 | SCMM Sample 2 | SCMM Sample 3 | SCMS[1] | STPP[2] Standard | Maleic Anhydride | Sodium Maleate | Sodium Glycolate |
|---|---|---|---|---|---|---|---|---|
|  |  |  | 11S | 30S2 |  |  |  |  |

[1] Made according to Netherlands application 701 7130
[2] Sodium tripolyphosphate
[3] Also contained singlets at 84. and 86.3 due to sodium glycolate and sodium acetate Detergency values compared to sodium trip olyphosphate were obtained with test fabric cotton in a Launder-Ometer test using detergent solutions made up with hard water and a commercial Naccanol (LABS) surfactant.

In the test procedure used standard wash solutions are prepared with detergent contents of 0.1, 0.1, 0.2 and 0.2% in about 3000 ppm hard water. The detergent composition is a 70/30 by weight mixture of builder (either STPP, SCMS or the ester-salt) and Nacconol 90F. The hard water was previously prepared by dissolving 26.43 grams $CaCl_2.2H_2O$ in 600 ml of distilled water and mixing this solution with a solution of 29.58 grams of $MgSO_4 \cdot 7H_2O$ in 600 ml of distilled water and making the admixed solutions up to 10 liters with distilled water.

Standard soiled coths containing the same amount of soil are placed in each solution and washed in a Launder-Ometer (1) for 10 minutes at 60° C. The cloths are removed from the wash solutions, rinsed, dried and the degree of whiteness measured by a Photovolt Reflectometer (2). The degree of whiteness of both soiled unwashed cloth and unsoiled unwashed cloth is also measured. The reflectance values from the washed soiled cloths obtained from both the 0.1 and 0.2% detergent solutions are averaged and the percent Detergency calculated:

$$\% \text{ Detergency} = \frac{Rsw - Rsu}{Ruu - Rsu} \times 100 \text{ where}$$

Rsw = average reflectance of washed soiled cloth
Rsu = reflectance of soiled unwashed cloth
Ruu = reflectance of unsoiled unwashed cloth The Detergency Coefficient is then calculated from the detergency of the test-salt and sodium tripolyphosphate:

$$\text{Detergency Coefficient, \%} = \frac{\% \text{ Detergency of test-salt}}{\% \text{ Detergency of Standard}} \times 100$$

(Standard = sodium tripolyphosphate)

1. The apparatus is designated Model B-5 Type LHD-HT by its distributer, Atlas Electric Devices CO., Chicago, Ill.
2. The apparatus used is the Photovolt Reflection Meter 670, Search Unit 610.W, sold by Photovolt Corporation, New York, New York.

Values of Detergency Coefficients obtained are given in Tables II and IV. It is noteworthy to remark that the sodium carboxymethyl maleate and the sodium carboxymethyl succinate are very slightly less effective than the nonbiodegradable sodium tripolyphosphate.

A crude (P113-7A) and a purified material (P113-10S+11S), 95% pure SCMM were evaluated and were comparable with the patented SCMS and were very slightly below the standard (a 90% performance being considered equivalent for the present purposes).

It is important to note that the SCMM appeared less sticky than the SCMS so it apparently did not hydrate as readily. According to the literature, SCMS has to be treated with water-ethanol to completely hydrate it in order to make it more easily handled but advantageously this step is not necessary with SCMM builder of the invention.

The preparation of additional ester-salts was carried out by the reaction of other dicarboxylic acid anhydrides with sodium glycolate in methyl ethyl ketone. Experimental conditions are summarized in Table III.

Besides crude sodium carboxymethyl succinate (SCMeS, insoluble in methyl ethyl ketone) products soluble in the methyl ethyl ketone were obtained among which, basis nuclear magnetic resonance, appears to be carboxymethyl succinic acid. The crude SCMeS was contaminated with starting materials but was purified by recrystallization from acetone. The salt and the acid were characterized by nuclear magnetic resonance as indicated in Table IV, multiplets forming in the

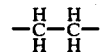

region and singlets in the

region but shifted from the singlet for sodium glycolate. The sodium analyses given in Table IV confirm that reactions to form the disodium salt comparable to those in equations 2 and 3, above, probably took place.

Also, as above, detergency values compared to sodium tripolyphosphate were obtained with test fabric cotton in a Launder-Ometer test using detergent solutions made up with hard water and Naccanol 90F. As shown by data in Table IV the purified SCMeS (P360-25SA + 16 AA) was very slightly below the standard.

With the other anhydrides listed in Table III, ester-salts were obtained, but the products were not isolated. That reaction products were obtained is indicated by nuclear magnetic resonance data given in Table V. Product mixture showed spectra for starting materials as well as the spectra listed, assigned to and agreeing with the spectra for the ester-salts. In the cases of tetrahydrophthalate and hexahydrophthalate derivatives, two slightly separated singlets were obtained in the

region due to the

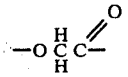

from the sodium glycolate addition. This is apparently due to the presence of isomers in the product.

TABLE III
PREPARATION OF OTHER CARBOXYMETHYL ESTER SALTS

| ANHYDRIDE Name | Formula | gms. | Sodium Glycolate gms. | Methyl-ethyl-ketone, ml. | Reaction Condition Temp. | Time. Hrs. | Work-up | Product Name | Product Formula | Amount (2) gms. | purity |
|---|---|---|---|---|---|---|---|---|---|---|---|
| Succinic anhydride | (succinic anhydride structure) | 10.2 | 10 | 200 | Reflux | 24 | Cooled, filtered MEK soluble recovered by evaporation and weighed 7.4 gms (1) | Sodium carboxymethyl succinate (SCMeS) | $H_2C-COONa$ <br> $H_2C-COOCH_2-COONa$ | 10.6 | 85 |
| Succinic anhydride | (succinic anhydride structure) | 10.2 | 12 | 200 | Reflux | 30 | Cooled, filtered. MEK soluble recovered by evaporation, wt. 7.5 gms (1) | Sodium carboxymethyl succinate (SCMeS) | $H_2C-COONa$ <br> $H_2C-COOCH_2-COONa$ | 14.3 | 83 |
| o-Phthalic anhydride | (phthalic anhydride structure) | 15.1 | 10 | 200 | Reflux | 24 | cooled, filtered. Both MEK soluble and insoluble contained product plus starting materials or corresponding acids | Sodium carboxymethyl phthalate (SCMP) | (benzene ring with) $COONa$, $COOCH_2-COONa$ | Not estimated | — |
| cis-Δ⁴-tetrahydrophthalic anhydride (THPA) | (structure) | 15.5 | 10 | 200 | Reflux | 24 | Cooled filtered. Solids were hygroscopic and only about ⅓ product plus starting materials MEK soluble = THPA | Sodium carboxymethyl-tetra-hydrophthalate (SCMTP) | (cyclohexene ring with) $COONa$, $COOCH_2-COONa$ | 7.0 | — |
| hexahydrophthalic anhydride (HHPA) | (structure) | 15.7 | 10 | 200 | Reflux | 24 | Cooled, Filtered Solids about ⅓ product plus ⅔ sodium glycolate. MEK-soluble mix of HHPA and carboxymethyl hexahydrophthalic acid | Sodium carboxymethyl hexahydrophthalate (SCMHP) | (cyclohexane ring with) $COONa$, $COOCH_2-COONa$ | 4.2 | — |

| Anhydride | Run No. |
|---|---|
| Succinic anhydride | P360-16 |
| Succinic anhydride | P360-25 |
| o-Phthalic anhydride | P360-19 |
| cis-Δ⁴-tetrahydrophthalic anhydride (THPA) | P360-17 |
| cis-hexahydrophthalic anhydride (HHPA) | P360-18 |

(1) Mixture of sodium glycolate or glycolic acid, succinic anhydride and, apparently, carboxymethyl succinic acid.
(2) Estimated from NMR

TABLE IV
EVALUATION OF SODIUM CARBOXYMETHYL SUCCINATE AND RELATED MATERIALS

| Test | SCMeS Sample 1 | SCMeS Sample 2 | SCMeS Mix of 1 and 2 | SCMes 1 and 2 purified | Succinic anhydride | Carboxymethyl Succinic acid |
|---|---|---|---|---|---|---|
| Proton NMR (in $D_2O$) | $\delta$4.45 (s 2) $\delta$2.4–2.8 (m4) | $\delta$4.45 (s2) $\delta$2.4–2.8 (m4) | — | $\delta$4.45 (s2) $\delta$2.4–2.8 (m4) | $\delta$2.6 (s) | $\delta$4.6 (s2) $\delta$2.6–2.8 (m4) (1) |
| Sodium, % (Found) | 17.5 | 22.7 | — | 20.6 | — | — |
| (theory) (for disodium salt) | 20.9 | 20.9 | — | 20.9 | — | — |
| Detergency Coefficient, % | — | — | 81.2 | 89.4 | — | — |
| Identification No. | P360-16A | P360-25S | P360-25S + 16A | P360-25SA + 16AA | | |

(1) Also contained singlets at $\delta$2.6 and $\delta$3.9 due to succinic anhydride or sodium succinate and sodium glycolate.
(2) See Table II for additional comparative data on STPP (standard) and sodium glycolate

TABLE V
NMR DATA ON DERIVATIVES OF CYCLIC ANHYDRIDES

| Test | Sodium Carboxymethyl Phthalate | Phthalic anhydride | Sodium Carboxymethyl tetrahydrophthalate | Tetrahydrophthalic anhydride | Sodium carboxymethyl hexahydro- Phthalate | Hexahydrophthalic anhydride | Sodium Glycolate |
|---|---|---|---|---|---|---|---|
| Proton NMR (in $D_2O$) | $\delta$7.3–7.7 (m4) $\delta$5.7 (s2) (1) | $\delta$8.0 (in $CCl_4$) | $\delta$5.62–5.77 (s(?)) (t-2) $\delta$4.4–4.5 (2s) $\delta$2.95–3.25 (m) $\delta$2.2–2.5 (t) (2) | $\delta$5.7 (2s 2) $\delta$3.0–3.2 (m2) $\delta$2.3–2.7 (d 4) | $\delta$4.33–4.4 (n 2) $\delta$2.7–3.0 (m 2) $\delta$1.6–2.1 (m 4) $\delta$1.25–1.6 (m 4) (1) | $\delta$3.05–3.35 (s 2) $\delta$3.75–2.15 (m 4) $\delta$1.6–1.75 (m 4) | 4.0 |

(1) Product contaminated with sodium glycolate
(2) Product contaminated with sodium glycolate and charge anhydride In another embodiment of the invention, maleic anhydride was treated with sodium isethionate (sodium hydroxy ethyl sulfonate, $HOCH_2CH_2SO_3Na$). A reaction occurred but yields were low. For example, when 10 grams maleic anhydride, 14 grams sodium isethionate and 200 ml. methyl ethyl ketone were refluxed together for 24 hours 14.4 grams of material was obtained that was a mixture of product and unreacted sodium isethionate (Basis NMR):

|  | Sodium Sulfoethyl Maleate | Sodium Isothionate |
|---|---|---|
| NMR (in $D_2O$) | $\delta$3.2–3.4 (t) $\delta$4.45–4.5 (d or t) $\delta$6.3–6.5 (q) | $\delta$3.1–3.2 (t) $\delta$3.8–4.0 (t) |
| Estimated amount of product, per cent | 12 | 88 |

Also 8.8 grams maleic anhydride, soluble in methyl ethyl ketone, was recovered.

Some sodium sulfoethyl maleate was also obtained when the reaction was run in dimethyl sulfoxide.

It will be understood that detergent compositions in which the builders of the invention are incorporated to the amount of about 5 to 95% based on the weight of the total detergent composite will include conventional compounds generally used in such formulations. The major ingredients of these compositions are surface active agents, soil suspending agents, sequestrants, foam stabilizers, alcohols, coloring materials, thickening agents and hydrotropes.

Suitable surface active agents include anionic, nonionic, zwitterionic morpholytic surfactants and mixtures thereof, especially those normally used in the washing of laundry and other soiled articles. These are used in an amount ranging from about 5 to about 45% of the total composition.

The hydrotropes which may be used as solubilizing agents include aromatic sulfonates such as sodium and potassium xylene sulfonates. The conventional amount of hydrotrope used varies from about 1.5 to about 10 percent by weight of the detergent.

Thus a solid detergent incorporating the builders of this invention would consist, in percentage by weight of

| Water soluble surface active agents | 3.5 to 45% |
|---|---|
| Hydrotropes | 1.5 to 10% |
| Builders of the invention | 5 to 95% |

A liquid detergent incorporating the builders of the invention would consist of:

| $C_7$–$C_8$ linear alkylsulfonate hydrotrope | 3 to 9 wt. % |
|---|---|
| Fatty acid alkylolamide foam stabilizer | 0 to 5 wt. % |
| Linear alkylsulfonate detergent ($C_{11}$–$C_{19}$) | 5 to 10 wt. % |
| Builders of the invention | 15 to 20 wt. % |
| Water | Balance |

It is to be understood that the foregoing examples are presented by way of illustration and explanation and that the invention is not limited by the details of such examples.

The embodiments of the invention in which an exclusive property or privilege is claimed are defined as follows:

1. A detergent builder selected from the group consisting of sodium carboxymethyl phthalate, sodium carboxymethyl tetrahydrophthalate, sodium carboxymethyl hexahydrophthalate, sodium carboxymethyl maleate and sodium sulfoethyl maleate.

2. A detergent composition consisting essentially of 3.5 to 4.5 by weight of a water-soluble surface active agent selected from the group consisting of of anionic, zwitterionic, ampholytic surfactants and mixtures thereof, 1.5 to 10 percent by weight of a hydrotrope; and from about 5 to 95 percent by weight of the total composition of a builder as defined in claim 1.

* * * * *